United States Patent
Kagermeier et al.

(10) Patent No.: US 8,463,613 B2
(45) Date of Patent: Jun. 11, 2013

(54) SYSTEM FOR CONTROLLING A DIAGNOSIS AND/OR THERAPY SYSTEM

(75) Inventors: Robert Kagermeier, Nürnberg (DE); Dietmar Sierk, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 996 days.

(21) Appl. No.: 11/999,639

(22) Filed: Dec. 6, 2007

(65) Prior Publication Data

US 2008/0147398 A1 Jun. 19, 2008

(30) Foreign Application Priority Data

Dec. 14, 2006 (DE) .......................... 10 2006 059 144

(51) Int. Cl.
*G10L 15/22* (2006.01)
(52) U.S. Cl.
USPC ........................................................ 704/275
(58) Field of Classification Search
USPC .................... 704/275, 270; 224/183
See application file for complete search history.

(56) References Cited

U.S. PATENT DOCUMENTS

| | | | | |
|---|---|---|---|---|
| 5,970,457 A | * | 10/1999 | Brant et al. | 704/275 |
| 6,028,537 A | * | 2/2000 | Suman et al. | 340/988 |
| 6,278,975 B1 | * | 8/2001 | Brant et al. | 704/275 |
| 6,806,847 B2 | * | 10/2004 | Nixon et al. | 345/2.1 |
| 6,847,336 B1 | | 1/2005 | Lemelson et al. | |
| 6,945,503 B2 | * | 9/2005 | Cohen | 248/206.5 |
| 6,990,455 B2 | * | 1/2006 | Vozick et al. | 704/275 |
| 7,035,091 B2 | * | 4/2006 | Le et al. | 361/679.03 |
| 2002/0128846 A1 | * | 9/2002 | Miller | 704/275 |
| 2003/0209578 A1 | * | 11/2003 | Kathrein | 224/183 |
| 2006/0195324 A1 | * | 8/2006 | Birk et al. | 704/275 |
| 2008/0023508 A1 | * | 1/2008 | Harchol | 224/183 |

FOREIGN PATENT DOCUMENTS

DE 196 17 294 A1 11/1997

OTHER PUBLICATIONS

German Office Action dated Sep. 5, 2007 for DE 10 2006 059 144.5-35 with English translation.

* cited by examiner

*Primary Examiner* — Abul Azad
(74) *Attorney, Agent, or Firm* — Lempia Summerfield Katz LLC

(57) ABSTRACT

A system for controlling a diagnosis and/or therapy system is provided. The system may include a portable unit that includes at least one voice signal detection device and a transmission device for wireless transmission of data to a receiver unit of the diagnosis and/or therapy system. The portable unit includes a voice recognition unit that generates control signals depending on the voice signals arriving via the voice signal detection device. The control signals may be transmitted by the transmission device as commands.

17 Claims, 2 Drawing Sheets

SYSTEM FOR CONTROLLING A DIAGNOSIS AND/OR THERAPY SYSTEM

The present patent document claims the benefit of the filing date of DE 10 2006 059 144.5, filed Dec. 14, 2006, which is incorporated by reference.

BACKGROUND

The present embodiments relate to controlling a diagnosis and/or therapy system with a portable unit. The portable unit may include at least one voice signal recording device and a transmission device for wireless transmission of data to a receiver unit of the diagnosis and/or therapy system.

A medical diagnostic system or therapy system, such as an angiography system, may be used for interventional treatment of a patient. During the intervention, different system functions or parameters may need to be selected, changed or moved to specific device or table positions. The operator cannot generally do this manually since both of the operator's hands are being used for the intervention. A limited range of different functions can be operated using foot switches.

Assistants may be used to carry out the operator's commands. An apparatus with a portable unit for voice control may be used to control a therapy system. The portable unit has a voice signal detection device embodied as a microphone and a transmission device for wireless transmission of the voice data detected by the microphone. The transmission device transmits the voice data to a receiver unit of the therapy system. The voice data is transmitted by radio. The voice data is processed in a voice recognition unit that is implemented in the fixed, non-portable central processing unit of the therapy system. The voice recognition unit uses voice recognition software to extract commands from the received voice data of the user or of the operator.

A deterioration of the sound quality of the incoming voice data or voice signals at the receive unit may cause a reduced voice detection rate, which leads to delays, and in the case of an incorrectly detected command, can even endanger the health of the patient. Voice recognition may be improved by avoiding wireless transmission of the voice data or voice signals. The security of the overall diagnosis and/or therapy system may be increased.

SUMMARY AND DESCRIPTION

The present embodiments may obviate one or more of the drawbacks inherent in the related art. For example, in one embodiment, the portable unit may transmit control signals to a diagnosis and/or therapy system.

In one embodiment, an apparatus for controlling a diagnosis and/or therapy system includes a portable unit. The portable unit includes a voice recognition unit that creates control signals. The control signals depend on the voice signals arriving via a voice signal detection device. The control signals may be transmitted by a transmission device as commands. The transmission of voice signals or voice data is avoided.

In one embodiment, only short commands are transmitted over the wireless transmission link and not large volumes of data. A secured protocol may be used for the transmission.

Sound transmission signals may include any now known or later developed sound transmission signal. For example, the sound transmission signals may be analog (e.g., AM or FM radio signals) or digital. The transmission signals may be compressed or uncompressed.

The voice recognition unit may include a processing unit with voice recognition software. The processing unit may assign commands from a catalog to the voice signals. For example, a portable unit may be a PDA-based processing unit or another electronic device weighing at most a few hundred grams, such as the weight and format of a mobile telephone.

The voice signal detection device may include a microphone or a data or signal input for the voice signals, depending on the design of the apparatus. A secure protocol may be used for the wireless transmission between the portable unit and the receiver unit. The wireless transmission may be, for example, by radio, by infrared signal, or by ultrasound.

In one embodiment, the apparatus may include an actuation element to enable the execution of safety commands. Inadvertent initiation of safety commands may be avoided. The operator or user must intentionally enable the transmission or execution. Transmission or execution cannot occur if the operator does not explicitly wish (enable) it. Safety functions may include, for example, radiation, device movement, or shockwave initiation. If the actuation element is a manually-controlled actuation element, it can also be ensured that the relevant hand of the operator is not on the patient.

The actuation element may include a two-stage safety switch with two independently actuatable contacts. The two-stage safety switch may satisfy SIL-2-conformant safety architecture.

In one embodiment, the actuation element may be integrated into the portable unit. The actuation element may be a foot switch. The portable unit may not be immediately accessible for the operator but, for example, may be arranged underneath a sterile coat.

The transmission device may transmit the commands at least twice. This may be part of a safety protocol. An incorrect transmission and an associated danger for the patient and the operator may be safely avoided.

The voice signal detection device includes a microphone. The microphone may be commercially-available and easy-to-disinfect. The microphone may be connected to a headset. The microphone may be positioned in front of or next to the mouth of the operator. The portable unit may be freely positioned, for example, on the operator's belt.

In one embodiment, the voice signal detection device includes a microphone integrated into a housing of the portable unit. The voice recognition unit is fixed to the voice signal detection device. The fixed connection may obtain optimum matching between the microphone and the voice recognition unit.

In one embodiment, the voice signal detection device includes a flexible tubular connecting section. The flexible tubular connecting section may connect the microphone to a housing of the portable unit. The microphone may be optimally positioned for the user. The optimal position may optimize the acoustic path, which cause an improvement in voice recognition.

In one embodiment, the portable unit includes an attachment device. The attachment device may include at least one securing device. The securing device may secure the portable unit in the user's surroundings. The portable unit may be positioned by the user in the environment, for example, on a device, such as an image amplifier or an x-ray device. The user places the device at a desired position that they have selected or at a position optimized for voice reception. The device may not impede the intervention. The unit may be attached to the user, for example, to a protective coat.

The attachment device may be, for example, an adhesive, Velcro tape, or similar device. In another example, the attachment device is a permanent magnetic element.

The attachment device may use a magnetic retaining force. The portable unit may be enclosed in a sterile package, for example, in a bag, without there being any significant diminution in the retaining force. The attachment may be a Velcro fastening. A partly sterile packaging be achieved with a Velcro fastening. As an alternative to the attachment or to provide further support, the portable unit may be attached using a neckband.

The attachment device may be a magnetic foil. The attachment device may be flat and flexible. The attachment connection may be supplemented by a self-adhesive magnetic foil for attachment. The magnetic foil may be omitted, for example, if a device in its environment, such as an image amplifier or an x-ray device, has ferromagnetic characteristics. This type of attachment to a user's or operator's radiation protection jacket with ferromagnetic characteristics is also made possible.

The portable unit may include at least one clip. The at least one clip may attach the portable unit to a user's belt. The at least one clip may be used to attach the portable unit to another item of clothing, for example, a pocket or pants waistband. The portable unit may be attached to a belt and a headset may be connected to the voice signal detection device, such as a linear microphone input.

The portable unit may include a receiver unit for wireless reception of signals. The portable unit may be used to detect and send instructions of the operator and to transmit information to the operator. For example, signals may be transmitted that confirm the receipt of a command and/or that alert the operator to specific dangers.

In one embodiment, the portable unit includes a voice synthesis system for synthesizing voice signals. The voice synthesis system may synthesize signals received via the receiver unit of the portable unit. The operator may be provided acoustically with a plurality of information without having to look away from the patient.

The present embodiments also relate to a system including a diagnosis and/or therapy system with a receiver unit and an apparatus for controlling the diagnosis and/or therapy system with a portable unit as described above.

In one embodiment, a method for controlling a diagnosis and/or therapy system is provided. The diagnosis and/or therapy system may include features or elements discussed above. For example, the system may include a portable unit with a voice recognition unit. The voice recognition unit creates control signals depending on the incoming voice signals via the voice signal detection device within the portable unit. The control signals are transmitted by a transmission device to the receiver unit. Wireless transmission of voice signals is avoided. By avoiding the wireless transmission of voice signals, the voice recognition may be improved and the safety of the entire diagnosis and/or therapy system may be increased. Since only short commands are transmitted over the wireless transmission link and not large volumes of data, the transmission may be undertaken without any great effort with a secured protocol.

DETAILED DESCRIPTION

Figure 1:
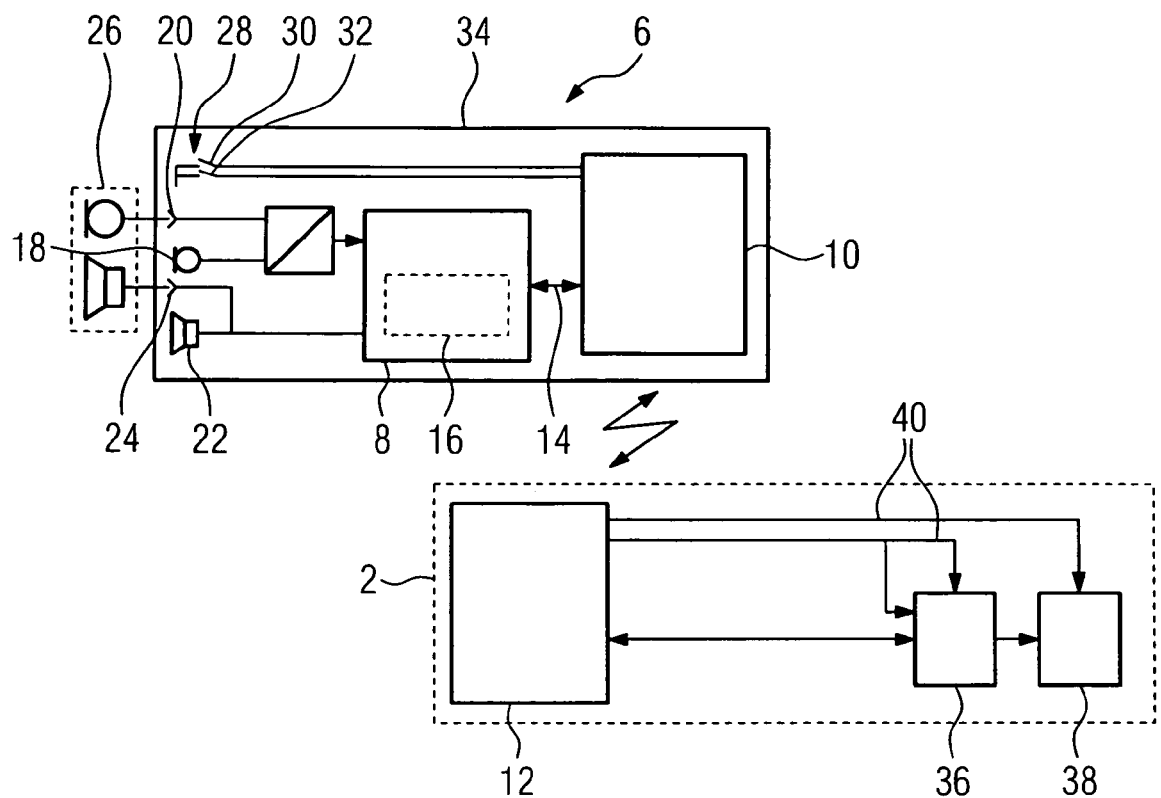
FIG. 1 a schematic diagram of one embodiment of a system including a portable unit and a receiver unit of an apparatus for controlling a diagnosis and/or therapy system.

FIG. 1 shows an apparatus for controlling a diagnosis and/or therapy system 2. The apparatus includes a portable unit 6 for control and activation of the diagnosis and/or therapy system 2. For example, the diagnosis and/or therapy system 2 may be an angiography system. To control or activate the diagnosis and/or therapy system 2, the user or operator 4 (see FIG. 3a-3d) can issue spoken commands, for example, to raise or lower a patient bed, to start an x-ray radiation of the patient, to change a recording angle or a section of an x-ray recording, or other similar commands. The spoken commands are detected, and the diagnosis and/or therapy system 2 executes the commands automatically.

The portable unit 6 may include a voice recognition unit 8. The voice recognition unit 8 may detect commands. The voice recognition unit 8 may be, for example, a DSP (Digital Signal Processor) platform or PDA (Personal Digital Assistant) processor platform with voice recognition software and a suitable operating system for portable pocket computers. In another example, the voice recognition unit 8 may, for example, be a processor with an Advanced RISC Machine (ARM) architecture.

The portable unit 6 may include a transmission device 10. The transmission device 10 may wirelessly transmit data to a receiver unit 12 of the diagnosis and/or therapy system 2. The data may be transmitted with a redundant safety protocol by radio. Alternatively, the data may be transmitted by Infrared or ultrasound signals. The redundant safety protocol transmits the commands twice. If the two versions transmitted do not match, there must be a transmission error and the command is not executed but instead a warning signal is created or a new transmission is initiated. The transmission device 10 and the voice recognition unit 8 are connected to each other via a standard data bus 14, for example, a RS232 data bus.

The transmission device 10 may be a receiver unit for wireless reception of signals. The transmission device 10 may receive signals sent by the stationary receiver unit 12. The transmission device 10 may use the same device for sending and receiving signals if the transmission is undertaken by radio.

The portable unit 6 may include a first voice signal detection device 18 and a second voice signal detection device 20. The first voice signal detection device 18 may be a linear microphone input and the second voice signal detection device 20 may be a fixed integrated microphone. The first voice signal detection device 18 and second voice signal detection device 20 are integrated into the portable unit 6 and are connected via a toggle switch to a data input of the voice recognition unit 8. The voice recognition unit 8 may generate control signals depending of the voice signals arriving via the voice signal detection devices 18, 20. The control signals are transmitted by the transmission device 10 as commands.

The portable unit 6 may include an integrated loudspeaker 22 and a loudspeaker output 24. The loudspeaker output 24 and the second voice signal detection device 20 may be connected to a headset 26. Without a headset 26, voice signals may be detected via the first voice signal detection device 18 and acoustic signals may be output via the integrated loudspeaker 22.

The voice recognition unit 8 may include a voice synthesis apparatus 16 for synthesizing voice signals from the signals received via the receiver unit of the portable unit 6. For example, the voice synthesis apparatus 16 may be the same or different processing unit as the voice recognition unit 8. The voice signals are output via the integrated loudspeaker 22 or via the loudspeaker output 24. The operator 4 may be supplied with information about the state of the diagnosis and/or therapy system 2 and/or with acoustic warnings.

The portable unit 6 may include an actuation element 28 for enabling the execution of safety-relevant commands. The actuation element 28 may be a safety switch with two SIL-2-conformant independently actuatable contacts 30, 32. The transmission device 10 transmits an enabling signal only when the two independently actuatable contacts 30, 32 are closed at the receiver unit 12.

Figure 2:
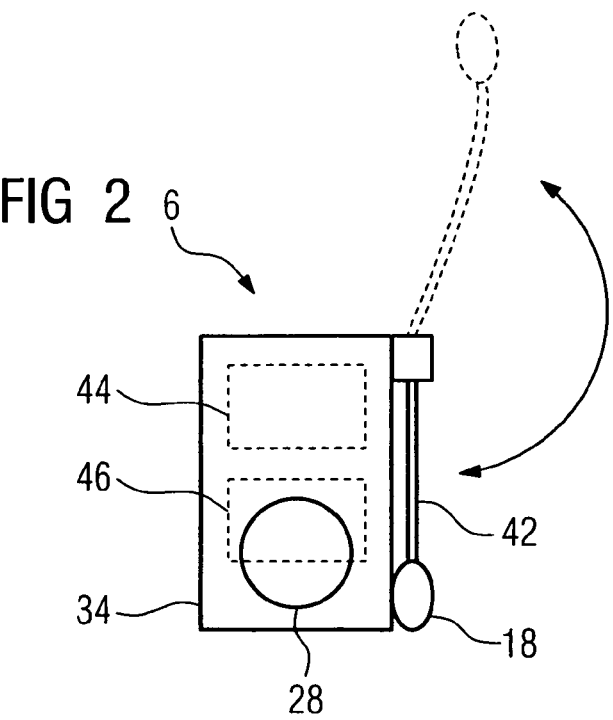
FIG. 2 illustrates one embodiment of the portable unit from FIG. 1 with a swiveling swan-neck microphone.

As shown in FIGS. 1 and 2, the portable unit 6 may include the actuation element 28. Alternatively, the actuation element 28 may be a foot switch. The foot switch may be connected via a cable to the portable unit 6 or to the receiver unit 12.

The elements of the portable unit 6, such as the voice recognition unit 8 and transmission device 10, may be disposed in a shared housing 34. The housing 34 may seal (protect) the said electronic components, for example, against spray water. The housing 34 is easy to disinfect from outside.

The receiver unit may receive data. The data received is transmitted to a control unit 36 via enabling lines 40. The control unit 36 may control an element 38 of the diagnosis and/or therapy system 2. The element 38 may be, for example, a radiation generator or a drive unit for moving a patient bed. A function of the element 38 or the element 38 and the control unit 36 of the receiver unit 12 may be enabled by an appropriate signal of the portable unit 6.

FIG. 2 shows the portable unit 6 or the housing 34 in a view from above. The actuation element 28 may be a large button, with a signal color. The first voice signal detection device 18 may be a microphone connected via a flexible, tubular connecting piece 42 to a housing 34 of the portable unit 6. The first voice signal detection device 18 or the connecting piece 42 may be pivoted inwards, such that it is parallel to a longitudinal edge of the housing 34. The first voice signal detection device 18 or the connecting piece 42 may be pivoted out, such that it is arranged optimally in relation to the user's or operator's 4 mouth. The first voice detection device 18 or the connecting piece 42 may be supported around an axis running in parallel to a transverse edge of the housing 34 of the portable unit 6 on the housing 34.

The portable unit 6 may include an attachment device 44. The attachment device 44 may be a permanent magnet element for securing the unit 6 to a protective jacket 48 of an operator 4. The attachment device 44 may be on the opposite side surface of the housing 34 to the actuation element 28. The attachment device 44 is shown as a dashed outline in FIG. 2. The attachment device 44 may be a magnetic foil. The magnetic foil enables the portable unit 6 to be attached to any other magnetic or magnetizable element, for example, to a radiation protection jacket of the operator 4, to a rail, a monitor stand or other similar device. The portable unit 6 may be enclosed in a sterile package, for example, in a plastic bag.

The portable unit 6 may include a clip 46. The clip 46 may be on the same side surface as the attachment device 44. The clip 46 may be used for attachment to a belt of an operator.

Figure 3A:
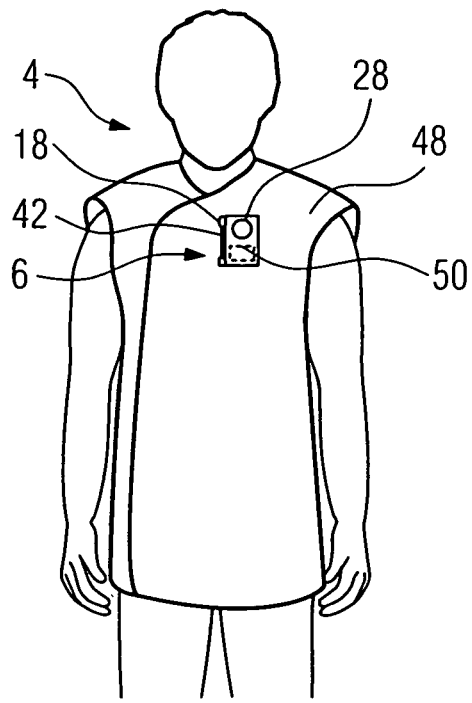
FIGS. 3a-3d illustrate different applications of the portable unit from FIG. 2.
Figure 3B:
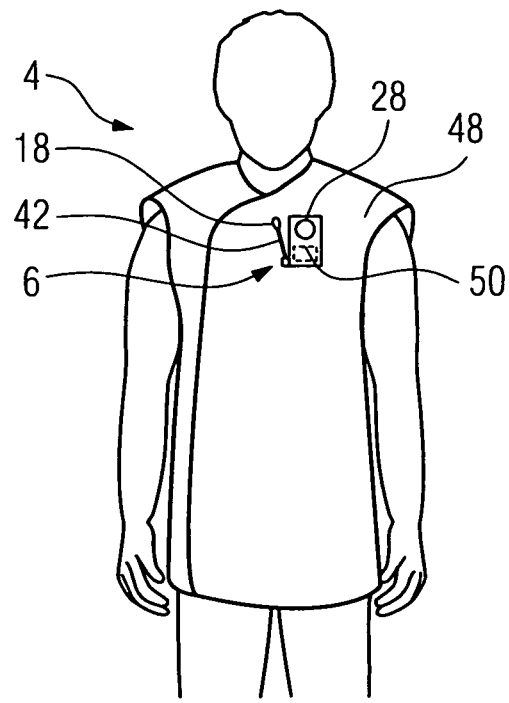
Figure 3C:
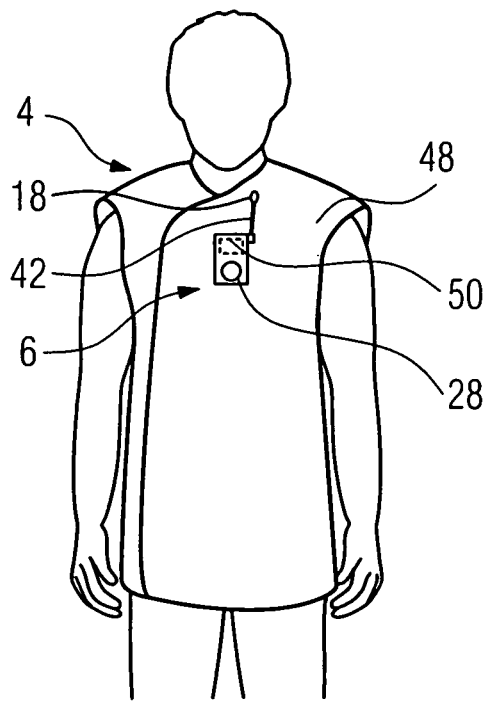

FIGS. 3a-3d illustrate applications for different arrangements of the portable unit 6 on the protective jacket 48 of the operator 4. As shown in FIG. 3a-3c, a self-adhesive magnetic foil 50 for attachment to the protective jacket 48 of the operator is glued to the outer surface of the protective jacket 48, just below the collar. The protective jacket 48 interacts with the attachment device 44 of the portable unit 6.

FIG. 3a shows a first application of the portable unit 6. The first voice signal detection device 18 is parallel to a longitudinal edge of the housing 34 of the portable unit 6. The portable unit 6 is below the collar of the protective jacket 48 of the operator 4 and is oriented so that voice signal detection device 18 is aligned upwards in the direction of the mouth of the operator 4.

FIG. 3b shows a second application of the portable unit 6. The first voice signal detection device 18, which is a swiveling swan-neck microphone, is bent away from the longitudinal edge of the housing 34 of the portable unit 6. The portable unit 6 is below the collar of the protective jacket 48 of the operator 4. The voice signal detection device 18 is aligned upwards in the direction of the mouth of the operator 4 so that the transverse edge, which is the edge in the vicinity of the actuation element 28, forms the upper edge of the housing 34.

FIG. 3c shows a third application of the portable unit 6. The first voice signal detection device 18 is a swan-neck microphone. The portable unit 6 is oriented so that the voice signal detection device 18 is aligned upwards in the direction of the mouth of the operator 4 so that the transverse edge, which is the edge in the vicinity of the actuation element 28, forms the lower edge of the housing 34.

Figure 3D:
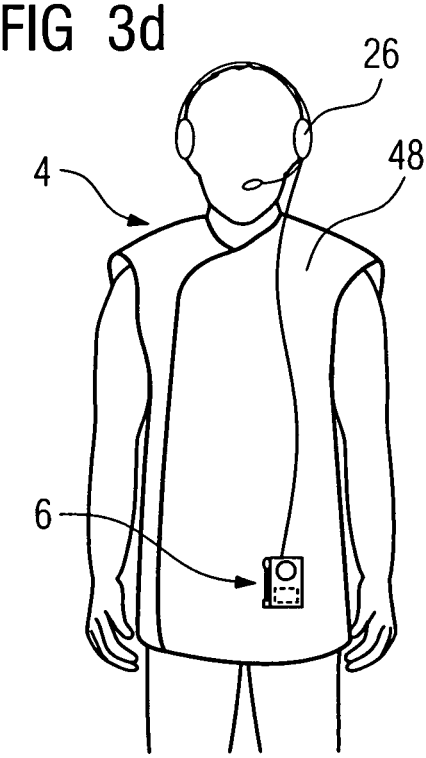

FIG. 3d shows a fourth application of the portable unit 6. The portable unit 6 is attached at a belt height on the protective jacket 48 of the operator 4. The operator 4 wears a headset 26 with headphones and a microphone. The microphone may be arranged directly in front of the operator 4's mouth. The headset 26 is connected via a cable to the second voice signal detection device 20 and to the loudspeaker output 24 of the portable unit 6.

The apparatus shown in FIG. 1-3 implements a method for control of the diagnosis and/or therapy system 2 with the portable unit 6, which includes a voice signal detection device 18, 20 and a transmission device 10 for wireless transmission of data to a receiver unit 12 of the diagnosis and/or therapy system 2.

The voice recognition unit 8 of the portable unit 6 may generate control signals. The control signals may depend on the voice signals arriving via the voice signal detection devices 18, 20, which are transmitted from the transmission device 10 to the receiver unit 12.

Various embodiments described herein can be used alone or in combination with one another. The forgoing detailed description has described only a few of the many possible implementations of the present invention. For this reason, this detailed description is intended by way of illustration, and not by way of limitation. It is only the following claims, including all equivalents that are intended to define the scope of this invention.

The invention claimed is:

1. A portable unit for controlling a diagnosis, therapy, or diagnosis and therapy system, the portable unit comprising:
   a voice signal detector operable to receive voice signals;
   a voice recognition unit operable to create control signals depending on the voice signals that arrive via the voice signal detector;
   a transmission device for wireless transmission of data to a receiver unit of the diagnosis, therapy, or diagnosis and therapy system, the transmission device being operable to transmit the control signals;
   a shared housing sized and shaped to be worn by a user, the voice signal detector, the voice recognition unit and the transmission device being disposed in the shared housing; and
   an actuation element configured to generate an enabling signal operable to enable execution of safety-relevant commands of the control signals when the actuation element is activated, such that the execution of the safety-relevant commands via the portable unit is only enabled when the actuation element is activated,
   wherein the transmitted control signals are for transmission to another controller, the another controller being of the diagnosis, therapy, or diagnosis and therapy system.

2. The portable unit as claimed in claim 1, wherein the actuation element includes a two-stage safety switch with two independently actuatable contacts.

3. The portable unit as claimed in claim 2, wherein the actuation element is integrated into the portable unit.

4. The portable unit as claimed in claim 1, wherein the transmission device is operable to transmit the control signals at least twice.

5. The portable unit as claimed in claim 1, wherein the voice signal detector includes a microphone input.

6. The portable unit as claimed in claim 1, wherein the voice signal detector includes a microphone integrated into a housing of the portable unit.

7. The portable unit as claimed in claim 1, wherein the voice signal detector includes a microphone connected by a flexible tubular connecting piece to a housing of the portable unit.

8. The portable unit as claimed in claim 1, comprising at least one attachment device operable to attach the portable unit in an environment of a user.

9. The portable unit as claimed in claim 8, wherein the attachment device includes a permanent magnetic element.

10. The portable unit as claimed in claim 9, wherein the attachment device includes a magnetic foil.

11. The portable unit as claimed in claim 10, wherein the magnetic foil includes a self-adhesive magnetic foil for attachment.

12. The portable unit as claimed in claim 1, comprising at least one clip operable to attach the portable unit to a belt of an operator.

13. The portable unit as claimed in claim 1, comprising a receiver unit operable for wireless reception of signals.

14. The portable unit as claimed in claim 13, comprising a voice synthesis apparatus operable for synthesizing voice signals received via the receiver unit of the portable unit.

15. A system for controlling a diagnosis, therapy, or diagnosis and therapy system, the system comprising:
  the diagnosis, therapy, or diagnosis and therapy system with a receiver unit; and
  an apparatus operable to control the diagnosis, therapy, or diagnosis and therapy system, the apparatus being a portable unit comprising:
    a voice signal detector operable to receive voice signals;
    a voice recognition unit operable to create control signals depending on the voice signals that arrive via the voice signal detector;
    a transmission device for wireless transmission of data to a receiver unit of the diagnosis, therapy, or diagnosis and therapy system, the transmission device being operable to transmit the control signals;
    a shared housing sized and shaped to be worn by a user, the voice signal detector, the voice recognition unit and the transmission device being disposed in the shared housing; and
    an actuation element configured to generate an enabling signal operable to enable execution of safety-relevant commands of the control signals when the actuation element is activated, such that the execution of the safety-relevant commands via the portable unit is only enabled when the actuation element is activated,
  wherein the transmitted control signals are for transmission to another controller, the another controller being of the diagnosis, therapy, or diagnosis and therapy system.

16. A method for controlling a diagnosis, therapy, or diagnosis and therapy system, the method comprising:
  generating control signals with a voice recognition unit of a portable unit sized and shaped to be worn by a user, the portable unit including a voice signal detection device, the control signals depending on voice signals being detected by the voice signal detection device;
  transmitting the control signals wirelessly to a receive unit of the diagnosis therapy, or diagnosis and therapy system; and
  generating, with an actuation element, an enabling signal operable to enable execution of safety-relevant commands of the control signals when the actuation element is activated, such that the execution of the safety-relevant commands via the portable unit is only enabled when the actuation element is activated,
  wherein the transmitted control signals are transmitted to a controller of the diagnosis, therapy, or diagnosis and therapy system.

17. A portable unit for controlling a diagnosis, therapy, or diagnosis and therapy system, the portable unit comprising:
  a voice signal detector operable to receive voice signals;
  a voice recognition unit operable to create control signals depending on the voice signals that arrive via the voice signal detector;
  a transmission device for wireless transmission of data to a receiver unit of the diagnosis, therapy, or diagnosis and therapy system, the transmission device being operable to transmit the control signals;
  a shared housing sized and shaped to be worn by a user, the voice signal detector, the voice recognition unit and the transmission device being disposed in the shared housing; and
  an actuation element configured to generate an enabling signal operable to enable execution of safety-relevant commands of the control signals when the actuation element is activated, such that the execution of the safety-relevant commands via the portable unit is only enabled when the actuation element is activated,
  wherein the transmission device is operable to transmit the control signals at least twice.

* * * * *